United States Patent
Choudary et al.

(10) Patent No.: US 6,706,901 B1
(45) Date of Patent: Mar. 16, 2004

(54) PROCESS FOR PREPARING TAXOL SIDE CHAIN USING HETEROGENEOUS TRIFUNCTIONAL CATALYST

(75) Inventors: Boyapati M. Choudary, Andhra Pradesh (IN); Naidu S. Chowdari, Andhra Pradesh (IN); Sateesh Madhi, Andhra Pradesh (IN); Lakshmi K. Mannepalli, Andrha Pradesh (IN); Jyothi Karangula, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/334,119

(22) Filed: Dec. 31, 2002

(51) Int. Cl.$^7$ ..................... C07D 305/14; C07D 493/00
(52) U.S. Cl. ...................................... 549/510
(58) Field of Search ......................... 549/510

(56) References Cited

PUBLICATIONS

Choudary et al., "A Trifunctional Catalyst for the Synthesis of Chiral Diols", Angewandte Chemie. International Edition., vol. 40, No. 24, 2001, pp. 4620–4623, XP001111757.
Donghyun et al., "Lipase–Catalyzed Transesterification as a Practical Route to Homochiral Syn–1,2–Diols. The Synthesis of the Taxol Side Chain", Tetrahedron Letters, vol. 39, 1998, pp. 2163–2166, XP004110658.
Beller et al., "First Efficient Palladium–Catalyzed Heck Reactions of Aryl Bromides with Alkyl Methacrylate", Tetrahedron Letters, vol. 37, No. 36, 1996, pp. 6535–6538, XP004030736.

Wang et al., "Large–Scale and Highly Enantioselective Synthesis of the Taxol c–13 Side Chain through Asymmetric Dihydroxylation", Journal of Organic Chemistry, vol. 59, No. 17, 1994, pp. 5104–5105, XP002248189.

Denis et al., "An Improved Synthesis of the Taxol Side Chain and of RP56976", Journal of Organic Chemistry., vol. 55, No. 6, 1990, pp. 1957–1959, XP002248190.

Okubo et al., "Heck Reactions in a Non–Aqueous Ionic Liquid Using Silica Supported Palladium Complex Catalysts", Tetrahedron Letters, vol. 43, 2002, pp. 7115–7118, XP004378312.

Beletskaya et al., "The Heck Reaction as a Sharpening Stone of Palladium Catalysis", Chemical Reviews, vol. 100, No. 8, 2000, pp. 3009–3066, XP002199991.

Kolb et al, "Catalytic Asymmetric Dihydroxylation", Chemical Reviews, vol. 94, No. 8, 1994, pp. 2483–2547, XP002248191.

*Primary Examiner*—Taofiq Solola
(74) *Attorney, Agent, or Firm*—Nixon & Vanderhye P.C.

(57) ABSTRACT

The present invention relates to an improved process for the preparation of taxol side chain by synthesizing (2R,3S)-2,3-dihydroxy-3-phenylpropionate with greater than 99% enantioselectivity and devoid of osmium even in crude form in a single pot using a recyclable multifunctional catalysts, conversion of diol obtained without further crystallization into bromoacetate, reaction of bromoacetate with $NaN_3$ in organic solvent followed by deacetylation with to obtain azido alcohol, benzoylation followed by hydrogenation of azido alcohol to obtain the (2R,3S)-(N-)-benzoyl-3-phenylisoserine methyl ester in 67% yield.

15 Claims, No Drawings

PROCESS FOR PREPARING TAXOL SIDE CHAIN USING HETEROGENEOUS TRIFUNCTIONAL CATALYST

FIELD OF THE INVENTION

The present invention relates to an improved process for the preparation of taxol side chain that comprises the following steps: (a) Synthesis of (2R,3S)-2,3-dihydroxy-3-phenylpropionate with greater than 99% enantioselectivity and devoid of osmium even in the crude in a single pot using recyclable multifunctional catalysts of the formula IE-IE-PdOsW, in which IE is a ion-exchanger comprising LDH, quaternary ammonium salt anchored on silica, clay, alumina, magnesia or resin (b) conversion of the diol thus obtained without further crystallization into bromoacetate using standard protocol, (c) reaction of bromoacetate with $NaN_3$ in DMF followed by deacetylation with NaOAc in MeOH affords azido alcohol (d) benzoylation followed by hydrogenation of azido alcohol gave the (2R,3S)-(N-)-benzoyl-3-phenylisoserine methyl ester in 67% overall yield.

BACKGROUND OF THE INVENTION

Taxol isolated from the bark of several yew species, is considered to be the most promising cancer chemotherapeutic agent and has been approved for the treatment of metastatic carcinoma of the ovary. Central to all synthetic strategies for taxol is the attachment of the C-13 side chain to the baccatin III nucleus. Since the presence of this side chain has proved to be essential for the biological activity of taxol, the development of short and practical synthetic routes for phenylisoserine derivatives, which are adaptable for industrial-scale production has become very important.

Sharpless et al. developed a process for the taxol side chain through AD of methyl cinnamate that led to 23% overall yield, but the diol needs to be recrystallized to enrich the ee. As the trifunctional catalyst in the present case afforded the diol with 99% ee using the $H_2O_2$ as a terminal oxidant, we present an efficient synthesis of taxol side chain starting from bromobenzene and methyl acrylate as shown in the Scheme 1. The treatment of diol(Methyl 2,3-dihydroxy-3-pheylpropionate) with HBr—AcOH yields broinoacelate, which in turn reacts with $NaN_3$ in DMF followed by deacetylation with NaOAc in MeOH to afford azido alcohol. Benzoylation followed by hydrogenation of azido alcohol gave the (2R,3S)-(N-)-benzoyl-3-phenylisoserine methyl ester in 67% overall yield. Reference is made to *J. Org. Chem* 1994, 59, 5104 wherein optically active taxol C-13 side chain was prepared using chiral auxiliary followed by bromo acetoxylation. The inherent disadvantage is use of homogeneous catalyst and low overall yield. Reference is also made to *Ind. J. Chem* 1995, 34B, 471 wherein optically active taxol C-13 side chain was prepared by asymmetric dihydroxylation using chiral auxiliary. The inherent disadvantage is recovery of entire amount of toxic osmium tetroxide used. Reference is made to *J. Org. Chem* 1990, 55, 1957 wherein optically active taxol C-13 side chain was prepared by asymmetric dihydroxylation using chiral auxiliary. The inherent disadvantage is recovery of entire amount of toxic osmium tetroxide used.

OBJECTS OF THE INVENTION

The main object of the present invention relates to an improved process for the preparation of taxol side chain by synthesizing (2R,3S)-2,3-dihydroxy-3-phenylpropionate with greater than 99% enantioselectivity and devoid of osmium even in crude form in a single pot using a recyclable multifunctional catalysts, conversion of diol obtained without further crystallization into bromoacetate, reaction of bromoacetate with $NaN_3$ in organic solvent followed by deacetylation with to obtain azido alcohol, benzoylation followed by hydrogenation of azido alcohol to obtain the (2R,3S)-(N-)-benzoyl-3-phenylisoserine methyl ester in 67% overall yield.

Another object of the invention to provide a novel and ecofriendly process for synthesis of (2R,3S)-2,3-dihydroxy-3-phenylpropionate from bromobenzene and ethylacrylate in a single pot.

It is another object of the invention to provide a process for the synthesis of (2R,3S)-2,3-dihydroxy-3-phenylpropionate dispensing with the use of soluble and toxic osmium tetroxide or potassium osmate dihydrate.

It is a further object of the invention to provide a process for the synthesis of (2R,3S)-2,3-dihydroxy-3-phenylpropionate wherein both the enantioselectivity and yields obtained are higher than reported in homogeneous dihydroxylation.

It is another object of the invention to provide a process for the synthesis of (2R,3S)-2,3-dihydroxy-3-phenylpropionate wherein the work-up procedure is simple and economical.

It is yet another object of the invention to provide a process for the synthesis of (2R,3S)-2,3-dihydroxy-3-phenylpropionate wherein the catalyst can be recycled several times with consistent activity.

It is another object of the invention to provide an environmentally safe process for the synthesis of (2R,3S)-2,3-dihydroxy-3-phenylpropionate by avoiding disposal problems.

SUMMARY OF THE INVENTION

Accordingly, the present invention provides a single pot process for the synthesis of taxol side chain comprising (a) synthesizing (2R,3S)-2,3-dihydroxy-3-phenylpropionate by in tandem or simultaneous Heck coupling of bromobenzene and methyl acrylate and N-oxidation of an amine in the presence of a cinchona alkaloid and using a recyclable multifunctional catalyst of the formula IE-IE-PdOsW, wherein IE is an ion-exchanger selected from the group consisting of LDH, quaternary ammonium salt anchored on silica, clay, alumina, magnesia and resin, (b) converting the diol obtained in step (a) without further crystallization into bromoacetate, (c) reacting the bromoacetate with $NaN_3$ in an organic solvent followed by deacetylation with NaOAc in another organic solvent to obtain an azido alcohol (d) subjecting the azido alcohol to benzoylation followed by hydrogenation to obtain the (2R,3S)-(N-)-benzoyl-3-phenylisoserine methyl ester.

In one embodiment of the invention, ratio of bromobenzene to methyl acrylate is 1:1.

In another embodiment of the invention, the organic solvent used in step (c) for reacting the bromoacetate with $NaN_3$ is DMF and the organic solvent used for deacetylation is MeOH.

In another embodiment of the invention, the selectivity of diol in step (a) is over 99%.

In a further embodiment of the invention, the multifunctional catalyst is recovered by filtration and reused for several cycles with consistent activity.

In another embodiment of the invention, the solvent selected for the multicomponent reaction is water, acetone, acetonitrile and t-butanol.

In another embodiment of the invention, the cinchona alkaloid comprises a chiral ligand selected from the group consisting of $(DHQ)_2PHAL$, $(DHQD)_2PYR$, $(DHQD)_2AQN$, DHQD-OAc, DHQD-CLB, DHQD-PHN, DHQD-MEQ, DHQD-IND and pseudoenantiomeric forms thereof.

In still another embodiment of the invention, the reactions are effected at a temperature in the range of −20 to +200° C. for a period 0.5 to 48 h.

In another embodiment of the invention, the base used for Heck-coupling is selected from triethylamine, tributylamine, potassium fluoride, and potassium acetate.

In yet another embodiment of the invention, amine used for N-oxidation is selected from the group consisting of N-methyl morpholine, trimethylamine and triethylamine.

In yet another embodiment of the invention, the quantity of multifunctional catalysts used in the reaction is 0.01 to 10 mol % of active species with respect to the substrate.

In another embodiment of the invention, the Heck coupling of bromobenzene and methyl acrylate and the in tandem or simultaneous N-oxidation of an amine is carried out with hydrogen peroxide in the presence of a cinchona alkaloid compound and in a solvent selected from the group consisting of water, acetone, acetonitrile and t-butanol and at a temperature in the range of −20 to +200° C. for a time period in the range of 0.5 to 48 h.

In an embodiment of invention, active species in catalyst ranges between 5 to 30%.

In an embodiment of the present invention, a process for the preparation of taxol side chain that comprises the synthesis of (2R,3S)-2,3-dihydroxy-3-phenylpropionate with greater than 99% enantioselectivity and devoid of osmium even in the crude in a single pot using recyclable multifunctional catalysts of the formula IE-PdOsW recently designed and developed, and conversion of the diol thus obtained without further crystallization into bromoacetate using standard protocol, which in turn reacts with $NaN_3$ in DMF followed by deacetylation with NaOAc in MeOH to afford azido alcohol. Benzoylation followed by hydrogenation of azido alcohol gave the (2R,3S)-(N-)-benzoyl-3-phenylisoserine methyl ester in 67% overall yield.

DETAILED DESCRIPTION OF THE PRESENT INVENTION

The novelty of the present invention lies in the preparation of taxol side chain that comprises the synthesis of (2R,3S)-2,3-dihydroxy-3-phenylpropionate with greater than 99% enantioselectivity and devoid of osmium even in the crude in a single pot using recyclable multifunctional catalysts of the formula IE-PdOsW, and conversion of diol obtained without further crystallization into bromoacetate using standard protocol. The bromoacetate in turn reacts with $NaN_3$ in DMF and is deacetylated with NaOAc in MeOH to afford azido alcohol. Benzoylation and then hydrogenation of azido alcohol gave (2R,3S)-(N-)-benzoyl-3-phenylisoserine methyl ester in 67% overall yield. Higher yields and enantioselectivities are obtained when multifunctional catalysts are used in the synthesis of (2R,3S)-2,3-dihydroxy-3-phenylpropionate The consistent activity and enantioselectivity obtained for several cycles in multicomponent reaction makes the process economical and commercially useful.

Scientific Explanation

The process of the invention for the preparation of taxol side chain comprises the following steps: (a) Synthesis of (2R,3S)-2,3-dihydroxy-3-phenylpropionate with greater than 99% enantioselectivity and devoid of osmium even in the crude, in a single pot using recyclable multifunctional catalysts of the formula IE-IE-PdOsW, in which IE is a ion-exchanger comprising LDH, quatemary ammonium salt anchored on silica, clay, alumina, magnesia or resin (b) conversion of the diol thus obtained without further crystallization into bromoacetate using standard protocol, (c) reaction of bromoacetate with $NaN_3$ in DMF followed by deacetylation with NaOAc in MeOH affords azido alcohol (d) benzoylation followed by hydrogenation of azido alcohol gave the (2R,3S)-(N-)-benzoyl-3-phenylisoserine methyl ester in 67% overall yield. (2R,3S)-2,3-dihydroxy-3-phenylpropionate which is the important intermediate for taxol side chain was synthesized using multifunctional catalysts in catalytic amount by tandem and/or simultaneous reactions involving Heck coupling, N-oxidation and asymmetric dihydroxylation of olefins employing hydrogen peroxide as terminal oxidant in presence of cinchona alkaloid compounds in a heterogeneous way.

The following examples are given by way of illustration and therefore should not be construed to limit the scope of the invention.

EXAMPLE 1

Preparation of Trifunctional Catalysts a) Preparation of LDH-PdOsW 1g of LDH was suspended in 100 mL of aqueous solution containing $Na_2PdCl_4$, $K_2OsO_4.2H_2O$ and $Na_2WO_4.2H_2O$ (0.3 mmol each) and stirred at 25° C. for 12 h under nitrogen atmosphere. The solid catalyst was filtered, washed thoroughly with 500 mL of water and vacuum dried to obtain 1.181 g of LDH-PdOsW (0.25 mmol $g^{-1}$ each of Pd, Os and W).

b) Preparation of Resin-PdOsW

Resin was obtained by quaternization of triethylamine (2.1 mL, 21 mmol) with 1 g of chloromethylated styrene-divinylbenzene copolymer (Merrifield resin, capacity ~2.1 mequiv/g) in chloroform (20 mL) under reflux for 24 h. 1 g of quaternary ammonium resin was suspended in 100 mL of aqueous solution containing $Na_2PdCl_4$, $K_2OsO_4.2H_2O$ and $Na_2WO_4.2H_2O$ (0.25 mmol each) and stirred at 25° C. for 12 h under nitrogen atmosphere. The solid catalyst was filtered, washed thoroughly with 500 mL of water and vacuum dried to obtain resin-PdOsW (0.2 mmol $g^{-1}$ of each Pd, Os and W).

c) Preparation of $SiO_2$—PdOsW

Modified silica was obtained by quatemisation of triethylamine (0.7 mL, 7 mmol) with bromopropylsilica (capacity 0.7 mequiv/g) in chloroform (20 mL) under reflux for 24 h. 1 g of quaternary ammonium silica was suspended in 100 mL of aqueous solution containing $Na_2PdCl_4$, $K_2OsO_4.2H_2O$ and $Na_2WO_4.2H_2O$ (0.11 mmol each) and stirred at 25° C. for 12 h under nitrogen atmosphere. The solid catalyst was filtered, washed thoroughly with 500 mL of water and vacuum dried to obtain $SiO_2$—PdOsW (0.1 mmol $g^{-1}$ of each Pd, Os and W).

EXAMPLE 2

Experimental Procedure for the Synthesis of Taxol Side Chain a) Synthesis of methyl (2R,3S)-2,3-dihydroxy-3-phenylpropionate LDH-PdOsW (0.4 g, 0.1 mmol), bromobenzene (10 mmol), methyl acrylate (10 mmol) and $Et_3N$ (11 mmol) were stirred at 70 4° C. for 16 h under nitrogen atmosphere. After completion of the Heck coupling, the heating was stopped and the reaction was allowed to reach room temperature. A mixture of (DHQ)₂PHAL (7.8 mg, 0.1 mmol) and NMM (0.5 g, 5 mmol) in ᵗBuOH—H₂O (5:1, 50 mL) was added in one portion to the reaction flask under stirring. H₂O₂ (30% aqueous, 15 mmol) was then slowly added over 15 h using a syringe pump. After the addition was complete, the stirring was continued for an additional 1 h and the catalyst was filtered and washed with ethyl acetate (100 mL). After removal of the solvent thus obtained crude material was chromatographed on silica gel using hexane/ethyl acetate (1:1) as an eluant to afford methyl (2R,3S)-2,3-dihydroxy-3-phenylpropionate (90% yield).

b) Synthesis of methyl(2R,3S)-2-acetoxy-3-bromo-3-phenylpropionate

The diol (2 mmol) was placed in a 25 mL single-necked round-bottomed flask followed by addition of 2.9 mL of 30 wt. % HBr—AcOH (13.2 mmol). The reaction mixture was heated at 45° C. for 30 min. Upon quenching with NaHCO₃ solution and extraction with ether, methyl(2R,3S)-2-acetoxy-3-bromo-3-phenylpropionate was obtained with 96% yield.

c) Synthesis of methyl(2R,3S)-3-azido-2-hydroxy-3-phenylpropionate

The acetoxy bromoester (1 mmol) and NaN₃ (1.5 mmol) in DMF (5 mL) were stirred at 50° C. for 12 h. After completion of the reaction, the solvent was removed, suspended in methanol and filtered through a pad of silica gel. The filtrate was stirred with NaOAc (10 mol %) for 12 h to afford methyl (2R,3S)-3-azido-2-hydroxy-3-phenylpropionate (85% yield).

d) Synthesis of (2R,3S)-(N-)-benzoyl-3-phenylisoserine methyl ester

A mixture of azido alcohol (0.5 mmol), benzoyl chloride, (1 mmol), Et₃N (2 mmol) and DMAP (0.03 mmol) in 5 mL of ethyl acetate was stirred at rt for 4 h, whereupon 1.4 mL of methanol was added. After being stirred for 3 h, the reaction mixture was treated with 10 mg of 10% Pd/C and stirred for 2 days under hydrogen atmosphere. Upon evaporation of the solvent, the crude product was purified by column chromatography to give (2R,3S)-(N-)-benzoyl-3-phenylisoserine methyl ester (92% yield).

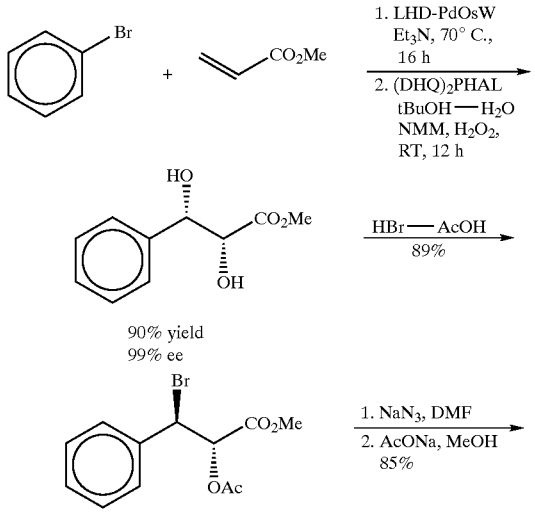

Scheme 1

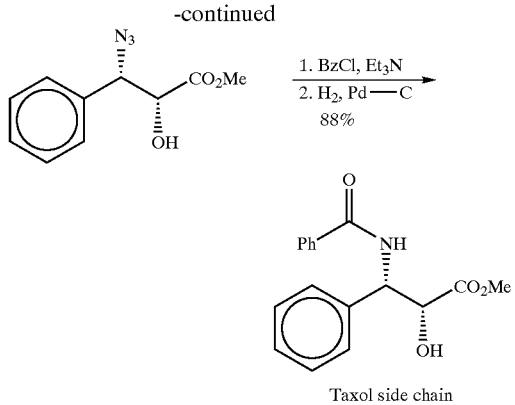

Taxol side chain

The main advantages of the present invention are:
1. A novel and ecofriendly process for the synthesis of taxol side chain starting from aryl halides and olefins using heterogeneous multifunctional catalyst is presented.
2. The present process dispenses the use of soluble, toxic osmium tetraoxide or potassium osmate dihydrate and instead we used heterogeneous reusable multifunctional catalysts to prepare (2R,3S)-2,3-dihydroxy-3-phenylpropionate. This catalyst is important in the sense that they are useful in catalyzing three different reactions by generating the precursors, prochiral olefins and NMO for AD reaction in-situ from the readily available cheaper starting materials such as methyl acrylate and bromobenzene and hence saves the energy and time, which are vital for a better and economical process.
3. Multifunctional catalysts are prepared and used as heterogeneous catalysts for synthesis of (2R,3S)-2,3-dihydroxy-3-phenylpropionate. The use of heterogeneous multifunctional catalysts precludes the presence of osmium in traces with product.
4. (2R,3S)-2,3-dihydroxy-3-phenylpropionate obtained using heterogeneous multifunctional catalyst was used in the synthesis of taxol side chain without any further crystallization.
5. Enantioselectivity and yields obtained are higher than reported in homogeneous dihydroxylation.
6. The work-up procedure is simple and economical.
7. The catalyst is subjected to many recycles, which displayed consistent activity.
8. The present process is environmentally safe since there is no disposal problem.

We claim:
1. A single pot process for the synthesis of taxol side chain comprising (a) synthesizing (2R,3S)-2,3-dihydroxy-3-phenylpropionate by in tandem or simultaneous Heck coupling of bromobenzene and methyl acrylate and N-oxidation of an amine in the presence of a cinchona alkaloid and using a recyclable multifunctional catalyst of the formula IE-IE-PdOsW, wherein IE is an ion-exchanger selected from the group consisting of LDH, quaternary ammonium salt anchored on silica, clay, alumina, magnesia and resin, (b) converting the diol obtained in step (a) without further crystallization into bromoacetate, (c) reacting the bromoacetate with NaN₃ in an organic solvent followed by deacetylation with NaOAc in another organic solvent to obtain an azido alcohol (d) subjecting the azido alcohol to benzoylation followed by hydrogenation to obtain the (2R,3S)-(N-)-benzoyl-3-phenylisoserine methyl ester.
2. A process as claimed in claim 1 wherein the ratio of the bromobenzene to the methyl acrylate is 1:1.
3. A process as claimed in claim 1 wherein the organic solvent used in step (c) for reacting the bromoacetate with NaN₃ is DMF.

4. A process as claimed in claim 1 wherein the organic solvent used for deacetylation in step (c) is MeOH.

5. A process as claimed in claim 1 wherein the selectivity of diol in step (a) is over 99%.

6. A process as claimed in claim 1 wherein the multifunctional catalyst is recovered by filtration and reused for several cycles with consistent activity.

7. A process as claimed in claim 1 wherein the reaction of step (a) is carried out using a solvent selected from the group consisting of water, acetone, acetonitrile and t-butanol.

8. A process as claimed in claim 1 wherein the cinchona alkaloid comprises a chiral ligand selected from the group consisting of $(DHQ)_2PHAL$, $(DHQD)_2PYR$, $(DHQD)_2AQN$, DHQD-OAc, DHQD-CLB, DHQD-PHN, DHQD-MEQ, DHQD-IND and pseudoenantiomeric forms thereof.

9. A process as claimed in claim 1 wherein the reactions of step (a) are effected at a temperature in the range of −20 to +200° C. for a period 0.5 to 48 h.

10. A process as claimed in claim 1 wherein the Heck-coupling is carried out using a base selected from the group consisting of triethylamine, tributylamine, potassium fluoride, and potassium acetate.

11. A process as claimed in claim 1 wherein the Heck coupling of bromobenzene and methyl acrylate and the in tandem or simultaneous N-oxidation of an amine is carried out with hydrogen peroxide in the presence of a cinchona alkaloid compound and in a solvent selected from the group consisting of water, acetone, acetonitrile and t-butanol at a temperature in the range of −20 to +200° C. for a period 0.5 to 48 h.

12. A process as claimed in claim 1 wherein the amine used for N-oxidation is selected from the group consisting of N-methyl morpholine, trimethylamine and triethylamine.

13. A process as claimed in claim 1 wherein the quantity of multifunctional catalysts used in the reaction is 0.01 to 10 mol % of active species with respect to the substrate.

14. A process as claimed in claim 1 wherein the active species in catalyst ranges between 5 to 30%.

15. A process as claimed in claim 1 wherein the catalyst is selected from the group consisting of LDH-PdOsW, resin-PdOsW and $SiO_2$—PdOsW.

* * * * *